(12) United States Patent
Shi et al.

(10) Patent No.: US 7,528,107 B2
(45) Date of Patent: May 5, 2009

(54) METHODS OF TREATING INFLAMMATION IN MAMMALIAN TISSUES COMPRISING ADMINISTERING HUMAN ALPHA-DEFENSINS

(75) Inventors: Jishu Shi, Auburn, AL (US); Shelly Aono, Auburn, AL (US); Wuyuan Lu, Ellicott City, MD (US)

(73) Assignee: Auburn University, Auburn, AL (US)

( * ) Notice: Subject to any disclaimer, the term of this patent is extended or adjusted under 35 U.S.C. 154(b) by 44 days.

(21) Appl. No.: 11/565,107

(22) Filed: Nov. 30, 2006

(65) Prior Publication Data

US 2008/0051333 A1    Feb. 28, 2008

Related U.S. Application Data

(60) Provisional application No. 60/740,991, filed on Nov. 30, 2005.

(51) Int. Cl.
*A01N 37/18* (2006.01)
*A61K 38/00* (2006.01)

(52) U.S. Cl. .................. 514/2; 514/12; 514/13
(58) Field of Classification Search ............. None
See application file for complete search history.

(56) References Cited

U.S. PATENT DOCUMENTS

| | | | |
|---|---|---|---|
| 5,242,902 A | 9/1993 | Murphy et al. | |
| 2004/0091498 A1 | 5/2004 | Zhang et al. | |
| 2006/0115480 A1* | 6/2006 | Hillman | 424/146.1 |

FOREIGN PATENT DOCUMENTS

| | | |
|---|---|---|
| JP | 2004 244378 | 9/2004 |
| WO | WO 03/070176 | 8/2003 |
| WO | WO 2005/013933 | 2/2005 |

OTHER PUBLICATIONS

Shi Jishu et al. (2006) "Inhibition of interleukin-1 beta release from monocytes by human alpha-defensins," Gastroenterology, vol. 130, No. 4, Suppl. 2.
Cunliffe R.N. (2003) "alpha-Defensins in the gastrointestinal tract," Molecular Immunology, vol. 40, No. 7, pp. 463-467.
Bevins, Charles L. (2005) "Events at the host-microbial Interface of the gastrointestinal tract—V. Paneth cell alpha-defensins in intestinal host defense," American Journal of Physiology, vol. 289, No. 2, pp. G173-G176.
"New Alpha-Defensin-3 and 5 Synthetic peptides available from peptides international" [Online] Apr. 4, 2005, website: URL: http://web.archive.org/web/20050404193557/http://pepnet.com/alphadefensins.html.

* cited by examiner

*Primary Examiner*—Robert Landsman
(74) *Attorney, Agent, or Firm*—Andrus, Sceales, Starke & Sawall, LLP

(57) ABSTRACT

Human α-defensins are inhibitors of interleukin-1β post transitional processing and release. Interleukin-1β is a key cytokine involved in the initiation and amplification of the inflammatory process, including the inflammation of diseases such as Crohn's Disease and Ulcerative Colitis. Particularly, human neutrophil defensin-1(HNP-1) produced mainly by neutrophils, and human α-defensin 5(HD-5) produced by Paneth cells has been found to block interleukin-1β post transitional processing and release. Thus, a pharmaceutical composition and method for treating inflammation in the mammalian tissues is herein disclosed. The pharmaceutical composition is a therapeutic supplementation of a metabolic pathway to reduce inflammation comprising a human α-defensins in a therapeutically effective amount or an amide, ester or salt thereof and a pharmaceutically effective carrier. The method for treating inflammation in mammalian tissues includes administering a human α-defensins to a mammal in an amount effective to inhibit the post translational processing and release of interleukin-1β.

6 Claims, 3 Drawing Sheets

A. α-defensins

```
PG-1    RGGRLCYCRRRFCVCVGR
HNP-1   ACYCRIPACIAGERRYGTCIYQGRLWAFCC
HD-5    ATCYCRTGRCATRESLSGVCEISGRLYRLCCR
Crp-3   LRDLVCYCRKRGCKRRERMNGTCRKGHLMYTLCCR
Crp-4   GLLCYCRKGHCKRGERVRGTCGIRFLY---CCPRR
```

B. Human β-defensins

```
hBD-1   DHYNCVSSGGQCLYSACPIFTKIQGTCYRGKAKCCK
hBD-2   GIGDPVTCLKSGAICHPVFCPRRYKQIGTCGLPGTKCCKKP
hBD-3   LQKYYCRVRGGRCAVLSCLPKEEQIGKCSTRGRKCCRRKK
```

Figure 1

METHODS OF TREATING INFLAMMATION IN MAMMALIAN TISSUES COMPRISING ADMINISTERING HUMAN ALPHA-DEFENSINS

CROSS-REFERENCE TO RELATED APPLICATIONS

This application claims the benefit of Provisional Application No. 60/740,991 filed Nov. 30, 2005, entitled Human Alpha-Defensins Inhibit Interleukin-1beta Release.

STATEMENT REGARDING FEDERALLY SPONSORED RESEARCH OR DEVELOPMENT

Not Applicable

BACKGROUND OF THE INVENTION

Inflammatory bowel disease or IBD includes Crohn's disease and Ulcerative Colitis and affects as many as one million Americans. IBD causes inflammation of the intestinal tract and particularly the intestinal wall, but Crohn's disease and Ulcerative Colitis differ in their location and depth of infection. Crohn's Disease was once considered a disease of only of the ileum, but is now recognized to affect any part of the digestive tract form the mouth to the anus. However, the ileum and the colon are the most commonly involved areas of the digestive tract with Crohn's disease. Meanwhile, Ulcerative Colitis is mainly considered a mucosal disease of the colon.

The clinical features of Crohn's Disease and Ulcerative Colitis demonstrate significant overlap including: abdominal pain, diarrhea, fever, and weight loss. These common symptoms suggest a commonality between the two diseases. One of the most prominent histological features observed in patients with these IBD diseases is infiltration of neutrophils, a type of white blood cell (granulocyte) that help the cell to kill and digest microorganisms it has engulfed by phagocytosis, into the inflamed mucosa at an early stage of inflammation. Disease activity is linked to an influx of neutrophils into the mucosa and the formation of crypt abscesses.

Interleukin-1 (IL-1; IL-1α and IL-1β) and interleukin-18 (IL-18; also known as interferon-γ inducing factor) are two key cytokines involved in the initiation and amplification of the inflammatory process of inflammatory bowel diseases such as Crohn's Disease and Ulcerative Colitis. IL-1 and IL-18 are central pro-inflamatory cytokines that function to stimulate the expression of genes associated with inflammation and autoimmune diseases. While monocytes, macrophages or monocytic cell lines are among the most studied cells in the known literature on the processing and release of IL-1 and IL-18, these cytokines are also expressed in various types of epithelial cells, including intestinal epithelial cells.

Cells exposed to IL-1 demonstrate a large expression of prostaglandin-E2 (PEG-2), platelet activation factor and nitric oxide (NO) due to the fact that IL-1 induces expression of cyclooxygenase type 2(COX-2), type 2 phospholipase A and inducible nitric oxide synthase (iNOS). IL-18 is a pivotal cytokine for the development of T-helper type I (Th1) lymphocyte responses. The most prominent activity of I1-18 is to induce interferon-γ (INFγ) by acting synergistically with IL-12. IL-18 also up-regulates the production of IL-1 and TNF-α.

It is known that increased gut mucosal secretion of IL-18 and IL-1β may predict an acute relapse of Crohn's Disease. It is also known that IL-18 and IL-1β positively correlates with the clinical severity of Ulcerative Colitis and Crohn's Disease. Serum IL-18 concentration is known to be significantly higher in patients with Crohn's disease than normal controls. Furthermore, animal studies have demonstrated that blocking IL-1 or IL-18 production and/or activity attenuates intestinal inflammation and tissue destruction due to IBD, see, Arnead, W. P., *Cytokine Growth Factor Rev.*, 13:323 (2002); Scheinin, et. al., *Clin. Exp. Immunol.*, 133:38 (2003); Lochner, et. al., *Pathobiology* 70:164 (2002); and Siegmund, B., *Biochem. Pharmacol.*, 64:1 (2002).

The genes for IL-1 and IL-18 do not encode a typical signal peptide and, as a result, newly synthesized proIL-1 and pro-IIL-18 are known to accumulate within the cytoplasm of activated monocytes, macrophages and intestinal epithelial cells. Conversion of the pro-forms of IL-1 and IL-18 to their mature form requires proteolytic action of caspase-1, see, Cerretti, et. al., *Science*, 257:97 (1992) and Akita et. al., *J. Biol. Chem.*, 272:26595 (1997). However, both caspase-1 dependent and caspase-1 independent IL-18 processing in epithelial cells have been reported, see, e.g. Lu et. al., *J. Immunol.* 165:1463 (2000); Sugawara, et. al., *J. Immunol.* 167:6568 (2001).

To achieve efficient IL-1 and IL-18 export from epithelial cells, such cells must encounter a secondary stimulus that specifically activates the posttranslational processing events. When a lipopolysaccharides (LPS) injection is followed with an Adenosine triphosphate (ATP) injection to the peritoneal cavity of mice, large quantities of cell-dissociated, mature IL-1β are generated. Likewise, it is known that cell-free IL-1 may be detected in plasma following LPS activation of human whole blood ex vivo, but cytokine levels are dramatically increased by co-administration of ATP. It is further known that cell death alone is insufficient to generate IL-1 or IL-18 posttranslational processing and release, maturations of these cytokines requires an active cellular response.

Accordingly, it has been revealed by several researchers that ATP initiates IL-1β/IL-18 posttranslational processing via ATP's activation of a $P2X_7$ receptor, see, Ferrari, et. al. *J. Immunol.*, 159:1451 (1997); Hogquist, et. al., *Proc. Natl. Acac. Sci. USA*, 88:8485; and Mehta, et. al., *J. Biol. Chem.*, 276:3820. However, it appears that the $P2X_7$ receptor is not an obligate element for IL-1β posttranslational processing and release since LPS-activated $P2X_7$ receptor$^{-/-}$ macrophages do not release mature IL-1β in response to subsequent ATP stimulation, and in fact, only release mature IL-1β when treated with nigercin, a non-relevant physiological stimulus. Thus, it is likely that other ligand(s) with higher affinity to the $P2X_7$ receptor or a different ligand receptor pathway initiates IL-1β/IL-18 posttranslational processing. Accordingly, no physiologically relevant effectors have been identified in the prior art that either promote or inhibit IL-1β/IL-18 posttranslational processing IL-18 posttranslational processing and release.

Defensins are endogenous antimicrobial peptides produced by white blood cells (neutrophils) and by cells lining the intestinal wall that aid in fighting bacterial infections (Paneth cells). Defensins also play a role in the inflammation of the intestines, commonly known as inflammatory bowel disease or IBD, including Crohn's Disease and Ulcertive Colitis. In fact, overproductions of defensins are characteristic of patients diagnosed with such diseases. Thus, increased local presences of antimicrobial defensin peptides are positively correlated with intestinal inflammation and damage in patients with Crohn's disease and Ulcerative Colitis.

Defensins comprise two classes: α-defensins (HNP1-3, HD-5, HD-6, Crp-3, Crp-4 and PG-1) and β-defensins (HBD-1, HBD-2 and HBD-3). As demonstrated in FIG. 1, defensin peptides contain six cysteine residues in a conserved spacing pattern. As further demonstrated in FIG. 1, the difference between α-defensins and β-defensins can be identified by the spacing and connectivity of their six cysteine residues. Defensins are amphiphilic in nature and have the ability to form voltage gated pores in phospholipid bilayers that allow defensins to perturb the membranes of susceptible microbial targets.

The isolation and purification of natural defensin peptides are well described in the scientific and patent literature. In particular, such methods are described in U.S. Pat. No. 5,242,902, as well as in U.S. Pat. Nos. 4,543,252; 4,659,692; and 4,705,777, the disclosures of which are incorporated herein by reference.

It is known that defensins are increased in the intestinal mucosa of patients with IBD, see, e.g. Fahlgren et. al. *Clin. Exp. Immunol.*, 131:90 (2003). HNP-1-3 have been detected in surface entrocytes of mucosa with active IBD, but not in controls suggesting that HNP-1-3 have the opportunity to interact with the lamina propria and with intestinal epithelial cells following loss of epithelial barrier integrity in IBD. Paneth cell produced α-defensins HD-5 and HD-6 have been found to be over 6 have been found to be over expressed in Crohn's disease patients and in the colonic mucosa of IBD patients.

Accordingly, although first identified as antimicrobial peptides, research has suggested that defensins can interact with host immune cells, thereby playing an important role in both innate and adaptive immune responses against bacterial infection. Furthermore, because defensins can also influence the function of epithelial cells, T cells, dendridic cells and monocytes, the role of defensisn in IBD is controversial. Nonetheless, the consensus from published data indicates that the presence of neutrophil and Paneth cell-derived α-defensins are increased in both Crohn's disease and Ulcerative Colitis.

SUMMARY OF THE INVENTION

It has surprisingly been found that human α-defensins, human neutrophil defensin 1 (HNP-1) produced mainly by neutrophils and human α-defensin 5 (HD-5) produced by Paneth cells, blocks LPS, ATP and *Staphylococcus aureus* alpha-toxin-mediated IL-1β release from human monocytes. HNP-1 and HD-5 are the first two endogenous inhibitors of IL-1β posttransitional processing and release.

Supplementation of metabolic pathways with HNP-1 and/or HD-1 in mammals suffering from inflammatory diseases is efficacious in treating inflammatory diseases including, but not limited to IBD (including Crohn's Disease and Ulcerative Colitis), rheumatoid arthritis, psoriasis and multiple sclerosis.

Accordingly, the present application contemplates the pharmaceutical composition for therapeutic supplementation of a metabolic pathway to reduce inflammation. Pharmaceutical composition comprises a human α-defensin in a therapeuticallically effective amount or an amide, ester or salt thereof and a pharmaceutically effective carrier. The human α-defensin may be either human neutrophil defensin 1 (HMP-1) or human α-defensin 5 (HD-5). However, it is contemplated that other α-defensins may be also therapeutically effective, particularly effective, particularly α-defensins produced by neutrophils or Paneth cells. The pharmaceutical composition is effective to have an inhibiting action on the release of interleukin-1β. Aforementioned, interleukin-1β is a central pro-inflammatory cytokine that stimulates the expression of genes associated with inflammation and autoimmune diseases.

The present application also contemplates a method for treating inflammation in mammalian tissues, the method comprising administering a human α-defensin to a mammal in an amount effective to inhibit the post translational processing and release of interleukin-1β. The method may comprise administering human neutrophil defensin 1(HNP-1) or human α-defensin 5(HD-5) to the mammal. However, it is contemplated that any α-defensin effective in treating inflammation produced by neutrophils or Paneth cells may be used. Most preferably, the mammal administered to in the method is a human.

BRIEF DESCRIPTION OF THE DRAWINGS

FIG. 1 demonstrates the primary amino acid structures of α-defensins and β-defensins, particularly defensins expressed in human intestinal mucosa. Conserved cystine residues in each group are indicated. In FIG. 1, the sequence for α-defensin PG-1 corresponds to SEQ ID NO: 1; the sequence for α-defensin I-HPN-1 corresponds to SEQ ID NO: 2; the sequence for α-defensin HD-5 corresponds to SEQ ID NO: 3; the sequence for α-defensin Crp-3 corresponds to SEQ ID NO: 4: the sequence for α-defensin Crp-4 corresponds to SEQ ID NO: 5: the sequence for Human βdefensin hBD-1 corresponds to SEQ ID NO: 6; the sequence for Human βdefensin hBD-2 corresponds to SEQ ID NO: 7; and the sequence for Human βdefensin hBD-3 corresponds to SEQ ID NO: 8.

DETAILED DESCRIPTION

Although it is well established that mutations in the Nod2 gene increase susceptibility to Crohn's Disease, the role of Nod2 in the pathogenesis of Crohn's Disease heretofore was elusive. Variants in Nod2 result in deficient intestinal intestinal expression of α-defensins and excessive secretion of IL-1β, causing increased inflammation. Thus, reduced intestinal expression of human α-defensins cause the over-production of IL-1β in patients with inflammatory complications.

Figure 2:
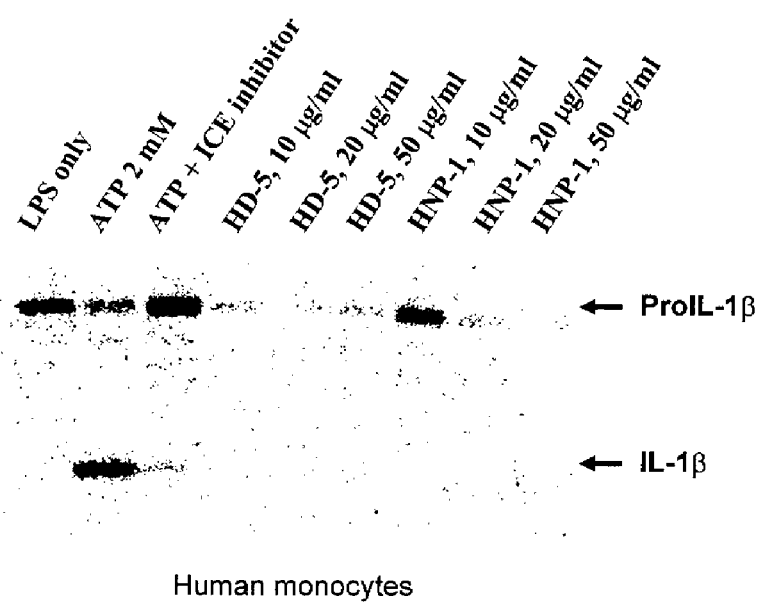
FIG. 2 demonstrates a western blot analysis of the inhibitory effect of HD-5 and HNP-1 on the production of proIL-1β and mature IL-1β proteins. The inhibition of such proteins will reduce inflammation.

Lipopolysaccharide (LPS) activated, $^{35}$S-methionine-labeled human monocytes treated with human α-defensins HNP-1 or HD-5 in the presence and absence of ATP were examined. Media and cell-associated fractions were harvested separately and IL-1β was recovered from each by immunoprecipitation. The resulting immuno-precipitates were analyzed by SDS-PAGE and autoradiography. Referring now to FIG. 2, in the absence of ATP, LPS activated monocytes released about 10% of $^{35}$S-methionine-labeled proIL-1β (31 kDa) into the media, but no mature (17 kDa) IL-1β was detected. As expected, addition of ATP to the LPS-activated monocyte culture led to the release of 90% of newly synthesized proIL-1β from the cell and more than 90% of the proIL-1β was processed to mature IL-1β and detected in the media.

Figure 3:
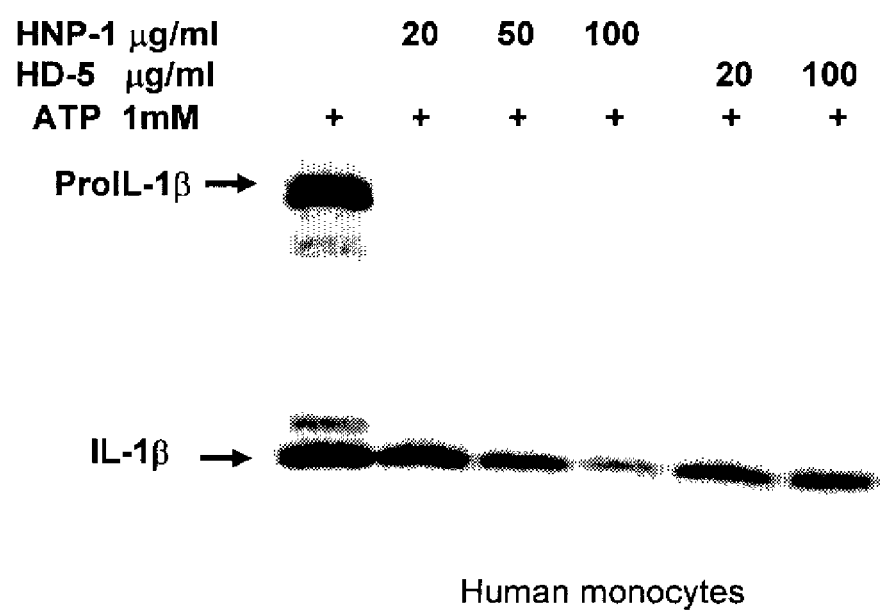
FIG. 3 demonstrates a western blot analysis of the inhibitory effect of HD-5 and HNP-1 on the production of proIL-1β in the presence of ATP. proIL-1β is blocked in a dose dependant manner.

Surprisingly, the release of proIL-1β from the LPS-activated monocyte culture was completely blocked by the addition of 10 ug/ml of HD-5, see FIG. 2. As further demonstrated in FIG. 2, 20 ug/ml of HNP-1 was also sufficient to block proIL-1β production. Further analysis demonstrated that of physiological concentrations of 5 ug to 100 ug/ml, both HNP-1 and HD-5 blocked ATP mediated proIL-1β release in a dose dependant manner. Of course, blocking proIL-1β prevents the production and release of mature IL-1β proteins. However, HNP-1 and HD-5 does not appear to affect the processing of proIL-1β after it is released extracellularly. Thus, if LPS-activated human monocytes are first treated with ATP, and then subsequently treated with α-defensins, some proIL-1β may escape extracellularly and be processed into mature IL-1β. FIG. 3 demonstrates this phenomenon. FIG. 3 also demonstrates that both HNP-1 and HD-5 blocked ATP mediated proIL-1β release in a dose dependant manner.

The inventors further investigated the role of α-defensins in IL-1β maturation in a murine model of colitis. After administration of 4% dextran sulfate sulfate sodium (DSS) in drinking water for 7 days to induce colitis, all MMP-7 knockout mice, which lack the mature intestinal α-defensins, died of severe intestinal inflammation and loss of body weight. Conversely, all wild-type control mice survived with only mild colitis and loss of body weight.

Thus, α-defensins function as a negative regulator of the posttranslational processing and release of IL-1β. In addition to their antimicrobial activity, α-defensins play an important role in inflammation by controlling the production of IL-1β. Accordingly the following therapeutic approaches are effective to reduce inflammation and tissue destruction.

A pharmaceutical composition for therapeutic supplementation of a metabolic pathway to reduce inflammation by blocking IL-1β release is desirable. The pharmaceutical composition may comprise a human α-defensin in a therapeutically effective amount, or an amide, ester or salt thereof and a pharmaceutically effective carrier. Pharmaceutically effective carriers include any and all solvents, disburse media, coatings, anti-bacterial and anti-fungal agents, isotonic and absorption delaying agents, and the like compatible with pharmaceutical administration. The use of media agents for pharmaceutically active substances is well known in the art.

Preferably, the pharmaceutical composition is orally administered; however the pharmaceutical composition may be injected or administered in any other manner suitable to effectively reduce inflammation. The pharmaceutical composition has an inhibiting action on the release of interleukin-1β through the supplementation of the human α-defensins in a therapeutically effective amount. In one embodiment of the invention, the human α-defensin is human neutrophil defensin 1(HNP-1). In another embodiment, the human α-defensin is human α-defensin 5(HD-5). However, it is contemplated that many human α-defensins produced by neutrophils or by Paneth cells may be effective to reduce inflammation when present in a pharmaceutically acceptable manner. The isolation and purification of natural defensin peptides are well described in the scientific and patent literature. In particular, such methods are described in U.S. Pat. Nos. 5,242,902; 4,543,252; 4,659,692; and 4,705,777 the subject matter of which are hereby incorporated by reference.

The present application also contemplates the method for treating inflammation in mammalian tissues. In the method, a human α-defensin is administered to a mammal in an amount effective to inhibit the post transitional processing release of interleukin-1β. The administration is preferably accomplished by injecting or orally administering a pharmaceutical composition to the mammal, however, it is contemplated that any other well-known methods of administering proteins to a mammal may be utilized. As noted above, the α-defensin that is administered is human neutrophil defensin 1(HNP-1) in one embodiment and human α-defensin 5(HD-5) in another embodiment. However, any α-defensin produced by neutrophils or Paneth cells that is effective to inhibit post transational processing is release of interleukin-1β is contemplated as being within the scope of this method. Preferably, the method for treating inflammation is carried out on a human; however any type of mammal may be subject of the administration.

The subject matter of the present application is further illustrated by the following examples which in no way should be construed as being further limiting. Contents of all cited references and patents cited throughout this application hereby expressly incorporated by reference.

EXAMPLES

Materials and Methods

Peripheral blood monocytes where isolated from healthy volunteers and patients with inflammatory bowel disease and suspended in monocyte maintenance medium (RPMI 1640 medium, 5% FBS 25 mM HEPES and 1% Pen/Strep). Blood samples from healthy volunteers were collected at the Auburn University Medical Clinic under an approved protocol. Blood samples from inflammatory bowel disease patients were provided by Dr. W. Park McGehee of of Internal Medicine Associates of Opelika, Ala., U.S.A.

Monocytes were first primed with lipopolysaccharides (LPS). Monocytes were allowed to adhere for two hours, after which medium supernatants were discarded. Attached cells were rinsed twice with maintenance medium and incubated in 1 ml of maintenance medium overnight at 37° C. in a 5% $CO_2$ environment. The following morning LPS was added to some walls to achieve a final concentration of 10 ng/ml and the cultures were activated for two hours at 37° C. The media was then removed and 1 ml of fresh medium (RPMI 1640 containing 1% FVS 25 mM HEPES and 5 mM $NaHCO_3$) was added to each well. These LPS-activated monocytes where then treated with ATP and subsequently, monocytes were selectively treated with α-defensins for interleukin-1β post transitional processing and release studies.

Human α-defensin HNP-1 was obtained from Peptide International of Louisville, Ky., U.S.A. Recombinant human α-defensin HD-5 was provided by Dr. Edith Porter of California State University, Los Angeles, U.S.A. The quality of the synthetic peptides were verified by their anti-bacterial activity. Synthetic human α-defensin HNP-1 was further purified by HPLC and compared to the natural HNP-1 by acid-urea PAGE. LPS-activated human monocytes were treated with 0, 1, 10 and 100 micrograms at 37° C. for three hours. It was also treated with 2 mm ATP for IL-1β maturation. Supernatants were then collected after a 5 minute centrifugation in microphage tubes. The concentration of mature IL-1β and the supernatants was quantified by ELISA(R&D Systems). Because the ELISA is reported by the manufacturer to recognize both pro and mature IL-1β species, presence of proIL-1β and mature IL-1β in the supernatant and cell lysates was also determined by western blot analysis. Briefly, proteins were precipitated from the supernatants by addition of trichloroacetic acid (TCA: 7.5% final concentration) and cholic acid (0.1% final concentration) to each sample. The percipate proteins were washed twice with 100% acetone to extract residual TCA and dissolved in 0.1 ml of SDS-PAGE sampled buffer. The cells where then washed once with PBS and lysed into 0.2 ml of lysis washed once with PBS and lysed into 0.2 ml of lysis buffer (25 mM HEPES 300 mM NaCl 1.5 mM $MgCl_2$, 0.2 mM EDTA, 1% triton X-100, 2 mg/ml leupeptin and 10 mg/ml PMF). Cell lysates and TSA precipitated proteins from the supernatants where then subjected to 12%

SDS-PAGE gels and then transferred to PVDV membranes for western blot analysis. IL-1β was probed with goat anti-IL-1β antibody and detected with the rabbit anti-goat IgG-horesradish peroxidase conjugate.

Results

As demonstrated in FIG. 2, HD-5 and HNP-1 operate to inhibit the production of proIL-1β for LPS activated human monocytes. Column 1, labeled "LPS Only" demonstrates that 4 million cell equivalents activated with 20 ng/ml of LPS and incubated for two hours produces proIL-1β proteins. Column 2 ("ATP 2 mM") demonstrates that four million cell equivalents are activated with 20 ng/ml LPS and further activated with 2 mM of ATP incubated for 3 hours produces less proIL-1β and significant amount of mature IL-1β protein. Column 3 ("ATP+ICE inhibitor") contains a control inhibitor (YVAD-CMK, 100 µM) for the ATP saturation path and, as demonstrated therein, 4 million cell equivalents treated with 20 ng/ml of LPS and further treated with ATP and with the CI inhibitor produces a substantial amount of proIL-1β, but no mature IL-1β proteins. Columns 4, 5 and 6 all demonstrate the effect of increasing an amount of HD-5 on 4 million cell equivalents activated with LPS. As demonstrated in columns 4, 5, 6, no proIL-1β nor any mature IL-1β proteins were expressed. Columns 7, 8, and 9 demonstrate the effect of HNP-1 on IL-1β expression. When 4 million cell equivalents are activated with 10 ng/ml of LPS and incubated for 2 hours and then treated with 20 mg/ml of HNP-1, some proIL-1β was displayed, but no mature IL-1β was demonstrated. The increase of 20-50 mg, represented by columns 8 and 9 demonstrate that no proIL-1β and no mature IL-1β proteins were produced.

FIG. 3 demonstrates that human α-defensins block the release of proIL-1β from ATP stimulated human monocytes. LPS-activated, $^{35}$S-methionine/cysteine-labeled human monocytes were treated with 1 mM ATP with or without HNP-1 or HD-5 for 3 hours. Media were harvested separately. IL-1β was recovered by immunoprecipitation. The resulting immunoprecipitates were analyzed by SDS-PAGE and autoradiography.

As demonstrated in FIG. 3, Column 1, when ATP alone is used to treat human monocytes, a substantial amount of both proIL-1β and mature IL-1β is produced. Columns 2-4 demonstrate that when 20-100 µg/ml of HNP-1 are added to ATP activated cells, no proIL-1β is released and mature IL-1β is inhibited in a dose dependant manner. Likewise, Columns 5 and 6 demonstrate that that when 20 and 100 µg/ml of HD-1 are added to ATP activated human monocytes, no proIL-1β is released and mature IL-1β is inhibited in a dose dependant manner. Since the α-defensins inhibit the release of proIL-1β in a dose dependant manner, the amount of proIL-1β that escapes extracellularly to mature into mature IL-1β is also reduced in a dose dependant manner. As aforementioned, HNP-1 and HD-5 does not appear to affect the processing of proIL-1β after it is released extracellularly.

Accordingly, the results of the experiments confirm that both HNP-1 and HD-5 block ATP mediated proIL-1β release in a dose dependant manner, and substantially completely block proIL-1β and mature IL-1β in LPS activated cells. Thus, α-defensins are a key inhibitor of Interleukin-1β release and have a substantial effect on reducing inflammation when used in a pharmaceutical composition or method of administering to a mammal.

Those skilled in the art will recognize, or will be able to ascertain using no more than routine experimentation, many equivalents to the specified embodiments of the invention disclosed herein. Such equivalents are intended to be encompassed by the following claims that particularly point out and distinctly claim the subject matter regarded as the invention.

What is claimed is:

1. A method for treating inflammation in mammalian tissues, said method comprising administering to a mammal in need thereof a human α-defensin in an amount effective to inhibit the posttranslational processing and release of interleukin-1 β.

2. The method of claim 1, wherein the human α-defensin is human neutrophil defensin 1 (HNP- 1).

3. The method of claim 1, wherein the human α-defensin is a human α-defensin 5 (HD-5) to the mammal.

4. The method of claim 1, wherein the human α-defensin is a human α-defensin produced by neutrophil cells to the mammal.

5. The method of claim 1, wherein the human αa-defensin is a human α-defensin produced by Paneth cells.

6. The method of claim 1, wherein the mammal is a human.

* * * * *

SEQUENCE LISTING

```
<160> NUMBER OF SEQ ID NOS: 8

<210> SEQ ID NO 1
<211> LENGTH: 18
<212> TYPE: PRT
<213> ORGANISM: Homo sapiens
<220> FEATURE:
<221> NAME/KEY: MISC_FEATURE
<223> OTHER INFORMATION: ALPHA DEFENSIN PG-1

<400> SEQUENCE: 1

Arg Gly Gly Arg Leu Cys Tyr Cys Arg Arg Arg Phe Cys Val Cys Val
1               5                   10                  15

Gly Arg

<210> SEQ ID NO 2
<211> LENGTH: 30
<212> TYPE: PRT
<213> ORGANISM: Homo sapiens
<220> FEATURE:
<221> NAME/KEY: MISC_FEATURE
<223> OTHER INFORMATION: ALPHA DEFENSIN HNP-1

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
```

```
                        20                  25                  30

<210> SEQ ID NO 3
<211> LENGTH: 32
<212> TYPE: PRT
<213> ORGANISM: Homo sapiens
<220> FEATURE:
<221> NAME/KEY: MISC_FEATURE
<223> OTHER INFORMATION: ALPHA DEFENSIN HD-5

<400> SEQUENCE: 3

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30

<210> SEQ ID NO 4
<211> LENGTH: 35
<212> TYPE: PRT
<213> ORGANISM: Homo sapiens
<220> FEATURE:
<221> NAME/KEY: MISC_FEATURE
<223> OTHER INFORMATION: ALPHA DEFENSIN Crp-3

<400> SEQUENCE: 4

Leu Arg Asp Leu Val Cys Tyr Cys Arg Lys Arg Gly Cys Lys Arg Arg
1               5                   10                  15

Glu Arg Met Asn Gly Thr Cys Arg Lys Gly His Leu Met Tyr Thr Leu
            20                  25                  30

Cys Cys Arg
        35

<210> SEQ ID NO 5
<211> LENGTH: 35
<212> TYPE: PRT
<213> ORGANISM: Homo sapiens
<220> FEATURE:
<221> NAME/KEY: MISC_FEATURE
<223> OTHER INFORMATION: ALPHA DEFENSIN Crp-4

<400> SEQUENCE: 5

Gly Leu Leu Cys Tyr Cys Arg Lys Gly His Cys Lys Arg Gly Glu Arg
1               5                   10                  15

Val Arg Gly Thr Cys Gly Ile Arg Phe Leu Tyr Phe Leu Tyr Cys Cys
            20                  25                  30

Pro Arg Arg
        35

<210> SEQ ID NO 6
<211> LENGTH: 36
<212> TYPE: PRT
<213> ORGANISM: Homo sapiens
<220> FEATURE:
<221> NAME/KEY: MISC_FEATURE
<223> OTHER INFORMATION: HUMAN BETA DEFENSIN hBD-1

<400> SEQUENCE: 6

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35
```

```
<210> SEQ ID NO 7
<211> LENGTH: 41
<212> TYPE: PRT
<213> ORGANISM: Homo sapiens
<220> FEATURE:
<221> NAME/KEY: MISC_FEATURE
<223> OTHER INFORMATION: HUMAN BETA DEFENSIN hBD-2

<400> SEQUENCE: 7

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40

<210> SEQ ID NO 8
<211> LENGTH: 40
<212> TYPE: PRT
<213> ORGANISM: Homo sapiens
<220> FEATURE:
<221> NAME/KEY: MISC_FEATURE
<223> OTHER INFORMATION: HUMAN BETA DEFENSIN hBD-3

<400> SEQUENCE: 8

Leu Gln Lys Tyr Tyr Cys Arg Val Arg Gly Arg Cys Ala Val Leu
1               5                   10                  15

Ser Cys Leu Pro Lys Glu Glu Gln Ile Gly Lys Cys Ser Thr Arg Gly
            20                  25                  30

Arg Lys Cys Cys Arg Arg Lys Lys
        35                  40
```